United States Patent [19]

Oakley

[11] Patent Number: 4,999,307
[45] Date of Patent: Mar. 12, 1991

[54] APPARATUS AND METHOD FOR PERIODIC ASEPTIC WITHDRAWAL OF LIQUID SAMPLES FROM A STERILE LIQUID SOURCE

[75] Inventor: Robert V. Oakley, Lafayette, Calif.

[73] Assignee: Baxter International Inc., Deerfield, Ill.

[21] Appl. No.: 310,539

[22] Filed: Feb. 13, 1989

[51] Int. Cl.⁵ .................. C12M 1/34; C12M 3/00; C12M 3/02; G01N 1/10
[52] U.S. Cl. .................................. 436/180; 128/762; 128/763; 128/765; 435/284; 435/286; 435/287; 435/289; 435/800
[58] Field of Search ............... 436/180; 422/103; 435/286, 287, 292, 293, 294, 295, 296, 800, 284; 128/762, 763, 764, 765, 766; 604/28, 30, 35, 36, 66, 191

[56] References Cited

U.S. PATENT DOCUMENTS

| | | | |
|---|---|---|---|
| 3,847,749 | 11/1974 | Smith et al. | 435/289 |
| 3,848,581 | 11/1974 | Cinqualbre et al. | 128/766 |
| 4,040,909 | 8/1977 | Libman et al. | 195/127 |
| 4,043,336 | 8/1977 | Kreb, III | 128/765 |
| 4,242,310 | 12/1980 | Greff et al. | 422/300 |
| 4,245,655 | 1/1981 | Patel | 128/765 |
| 4,453,574 | 6/1984 | Elliott | 435/287 |
| 4,658,655 | 4/1987 | Kanno | 128/766 |
| 4,689,306 | 8/1987 | Redikultsev et al. | 435/292 |
| 4,695,551 | 9/1987 | Samhaber et al. | 435/292 |
| 4,714,460 | 12/1987 | Calderon | 604/28 |
| 4,784,157 | 11/1988 | Halls et al. | 128/762 |
| 4,829,002 | 5/1989 | Pattillo et al. | 435/287 |

FOREIGN PATENT DOCUMENTS 2614542 2/1977 Fed. Rep. of Germany .

Primary Examiner—Robert J. Warden
Assistant Examiner—Kimberly A. Trautman
Attorney, Agent, or Firm—St. Onge Steward Johnston & Reens

[57] ABSTRACT

A liquid sampling device is provided for periodic aseptic removal of samples of a source liquid to be analyzed, comprised of a primary liquid conduit tube closed at one end and, at the other end, adapted to be in liquid communication with a principal or secondary flow line through which the source liquid flows or is arranged to flow, and a plurality of separate sample conduit tubes emanating from and in liquid communication with the primary liquid conduit tube, one end of each sample conduit tube being adapted to withdraw therethrough a sample of the source liquid. The device is configured such that, after a sample is taken through a particular sample conduit tube, that tube can be isolated or removed from the system, and subsequent samples are taken successively from remaining sample conduit tubes in the same manner.

2 Claims, 2 Drawing Sheets

APPARATUS AND METHOD FOR PERIODIC ASEPTIC WITHDRAWAL OF LIQUID SAMPLES FROM A STERILE LIQUID SOURCE

BACKGROUND OF THE INVENTION

The present invention relates to the sterile sampling of a liquid and, more particularly, to the periodic sterile withdrawal from a liquid flow path of a sample quantity of the liquid. In its most preferred respects, the invention relates to a method and apparatus for periodically effecting the sterile withdrawal of a sample of culture fluid utilized for the in vitro culture of animal cells.

In many systems for the in vitro culture of animal cells either for recovery of cell-secreted proteins therefrom or for other purposes such as growth of tissue-like masses or study of cellular interactions or the like, culture medium which is used to nourish the cells and to carry away cell-secreted products is continuously or intermittently fed to and withdrawn from the culture chamber through appropriate tubing, oftentimes in a recirculating closed loop system with provision for periodic or continuous replenishment of fresh culture medium.

It is well known that the monitoring of the culture medium in the culture unit and/or at one or more points in the flow path is a useful way for monitoring and controlling the culture process. Thus, for example, analysis of the medium before and after passage through the culture chamber for nutrient components and/or cell-secreted proteins and/or cell-secreted metabolites or the like can provide important information regarding the number of viable cells in the culture unit, the rates of nutrient consumption by the cells and the rate of product secretion, the cell growth rates, the particular stages of cell growth or subdivision, and the like, all of which can be used not only to monitor the system but to signal changes which might require alteration of process conditions, medium composition, or the like designed to optimize the culturation process.

Also well-known is the fact that the culturing process must be carried out under the strictest of aseptic conditions lest the cells, which are without the elaborate defense mechanisms generally provided by a typical in vivo animal environment, become contaminated, leading to contamination of products recovered therefrom and/or loss of cell viability. As a consequence, in vitro animal cell culture systems and their component parts are initiated and maintained under sterile conditions, with each portion or the entirety of the system being sterilized prior to commencement of the process, and using sterile culture medium and uncontaminated seed cell stocks.

The problem arises, then, of the need to insure that sampling of the culture medium or culture fluid be carried out in a manner which avoids introduction of contaminants into the pre-established sterile system. Prior known techniques for accomplishing this sterile withdrawal of liquid for sampling are, at best, elaborate, time-consuming and expensive, and at worst, ineffective. Generally, the area from which a liquid sample is to be taken, be it a culture vessel or a liquid flow line to or from a culture vessel, is provided with a sample port such as in the form of a short segment of tubing or other appropriate structure. The system is then invaded via this sample port to withdraw a quantity of liquid. Some techniques involve the use of an elastomeric septum in the sample port into which a sterilized needle, affixed to a syringe, is inserted and withdrawn. Such techniques are recognized as being far from ideal and run significant risk of introducing contaminants into the culture system via the sample port, particularly where the same sample port is used for repeated sampling. More sophisticated sampling techniques involve connection of a sample bottle or like container to the sampling port to permit a liquid sample to collect in the bottle, followed by removal of the bottle from the port for analysis of the collected liquid contents, all being effected through a series of complex valves or other suitable devices associated with the sample port and/or sample bottle. Still other techniques involve utilization of sterilizable connectors between the sample port and collection receptacle, wherein the connection is sterilized before and/or after the collection receptacle is affixed and removed, e.g., by flushing of the connector with a sterilizing gas.

As a consequence either of the inefficiency or complexity of known sampling techniques, not only is the risk of contamination present but there also may exist an inherent limitation on the number or frequency of samplings which can be accommodated, either by reason of a limited number of sterilizable sequences to which a particular connector can be subjected before severe degradation occurs or simply by reason of the inordinate amount of time needed to perform a sample withdrawal. This can pose significant problems in situations where rapid and frequent sampling is required in order to monitor a potentially fast-changing situation. Still further, of course, elaborate and/or time-consuming sampling techniques can add significantly to the overall cost of the culture process.

It is accordingly an object of the present invention to provide a method and apparatus for effecting the withdrawal of a liquid sample from a sterile liquid container or flow line, which permits of rapid and cost-effective performance of the sampling operation yet under conditions whereby the sterile environment is safeguarded. More specific objects of the invention are to provide a method and apparatus for sterile withdrawal of a sample of culture fluid from an on-going in vitro culturation of animal cells, be it from the culture chamber, flow lines leading to or from the culture chamber, or from other apparatus or flow lines associated with the culture system.

SUMMARY OF THE INVENTION

These and other objects as will be apparent are achieved by provision of a sterilizable liquid sampling device comprised of a primary liquid conduit tube, one end of which is adapted to be in liquid communication with the liquid source to be sampled, e.g., by connection to a principal flow line or by connection to a secondary flow line either branched off from the principal flow line or emanating from a vessel (e.g., a culture unit) whose liquid contents are to be analyzed, and the other end of which is closed to prevent escape of liquid therefrom. Emanating at pre-selected, spaced-apart points along the length of the primary liquid conduit tube (e.g., branched off therefrom) are a plurality of separate liquid sample conduit tubes. One end of each such sample conduit tube is adapted to be in liquid communication with the primary liquid conduit tube such that each sample conduit is adapted to receive a sample portion of liquid through the primary liquid conduit, which is representative of the liquid source with which the primary liquid conduit is in liquid communication. The other end of each sample conduit tube is adapted to provide an exit for liquid contained in or drawn through the sample conduit tube. In the preferred embodiment of the invention, the exit side of each of the sample conduits is open and in sealed liquid communication with means for removing a sample portion of liquid through the sample conduit and into a suitable receptacle therefor, most preferably a syringe having a withdrawable plunger arranged within a bore receptacle.

In operation, the sterilizable liquid sampling system of the invention is, by means of the end of the primary liquid conduit adapted to be in liquid communication with the liquid source to be sampled, affixed in a suitable manner to a principal or secondary flow line, as the case may be, through which the liquid source to be sampled flows or can be arranged to flow. In the course of a particular process, such as a culture process in which it is desired to periodically analyze, and thus monitor, the culture fluid emanating from the culture unit, that culture fluid, at any particular point in time in the process, is drawn into a sample conduit tube via flow through the primary liquid conduit. Once the liquid sample is removed from the exit end of the sample conduit tube, that tube is then isolated and/or removed from the remaining plurality of sample ports and from liquid communication with the primary liquid conduit tube, either by compressive clamping about the periphery of the sample conduit tube and/or about the periphery of the primary liquid conduit tube in the area where it is in liquid communication with the sample conduit tube, and then optionally physically severing the sample conduit tube or primary liquid conduit tube.

In this manner, a first sample of the liquid source to be analyzed can be taken through and from a first sample tube branched off from the primary liquid conduit tube which is in liquid communication with the liquid source. After the sample is drawn, the sample conduit tube is isolated or removed in a way which maintains a closed end of the primary liquid conduit tube and also maintains liquid communication between the primary liquid conduit tube and all remaining sample conduit tubes. Later, a next sample is taken through and from the next adjacent sample conduit tube in the same manner, and so on. As such, each sample conduit tube is used for a single sample, but a plurality of sample conduit tubes are provided so that any desired pre-arranged number of samples can be withdrawn.

The advantages of the present invention are many. By avoiding the need to continually withdraw liquid samples from a single port, the risk of introducing contaminants into the sterile liquid source being analyzed by virtue of such repeated invasions is eliminated. At the same time, repeated sampling of the source liquid is made possible by the simple expedient of providing a suitable number of sample conduit tubes in the assembly of the device. The unitary sampling device, with primary liquid conduit tube and sample conduit tubes, is made to be completely and easily sterilizable and, thus, once affixed as part of an overall sterile system, can be arranged to retain sterility even during sampling operations by suitable isolation of the sample conduit tube from the remainder of the system. Perhaps most importantly, the device is easy to assemble from relatively inexpensive materials and can be utilized without resort to elaborate means or inordinate skill.

DETAILED DESCRIPTION OF THE INVENTION

Figure 1:
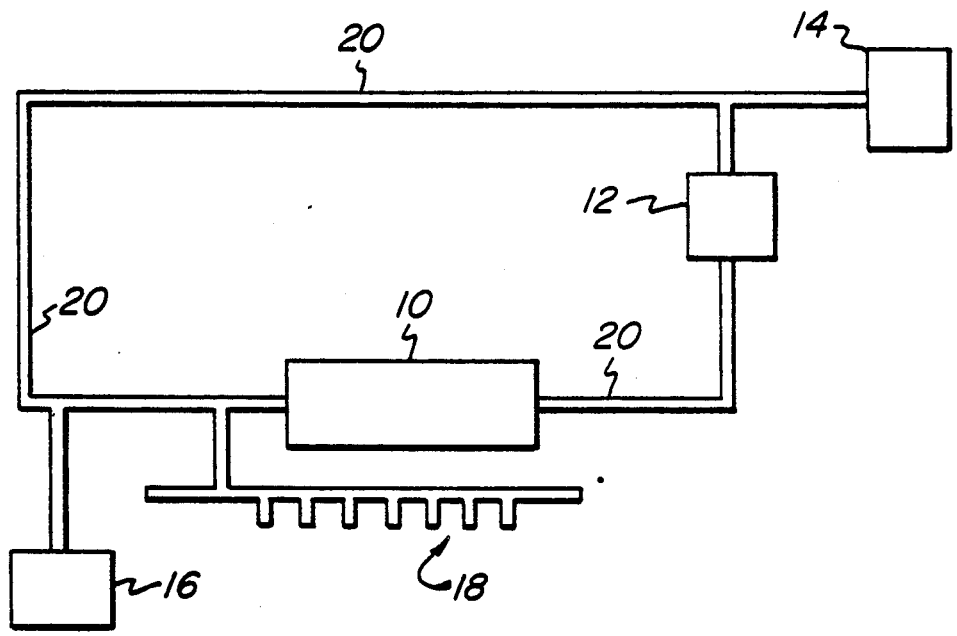
FIG. 1 is a schematic illustration of an in vitro animal cell culture system including the liquid sampling device of the invention.

With reference to FIG. 1, a typical arrangement for an in vitro animal cell culture system of the continuous perfusion type is shown comprised of a culture unit 10, an oxygenation means 12, a source of fresh culture medium 14, a product collection vessel 16, a liquid sampling device 18 according to the invention, and associated tubing 20 interconnecting the various components.

The components of the culture system are either sterilized en masse or separately sterilized and aseptically connected. An inoculum of the cells to be cultured is introduced into the culture unit 10, and a suitably oxygenated culture medium is used to nourish the cells in the culture unit and to carry away from the culture unit cell-secreted proteins, metabolites and the like.

One desirable location for periodic liquid sampling in such a system is at the exit from the culture unit as shown in FIG. 1. By monitoring, for example, particular nutrients or cell-secreted products or pH or the like, determination can be made regarding cell viability, cell number and the like, which in turn can be used to adjust or augment features of the system such as culture medium composition, oxygenation, flow rates and the like. For accurate monitoring of such parameters, it is necessary that sample contamination be avoided, that capability exist for repeated samples over time, and, of course, all in a manner which does not jeopardize the sterility of the system.

Figure 2:
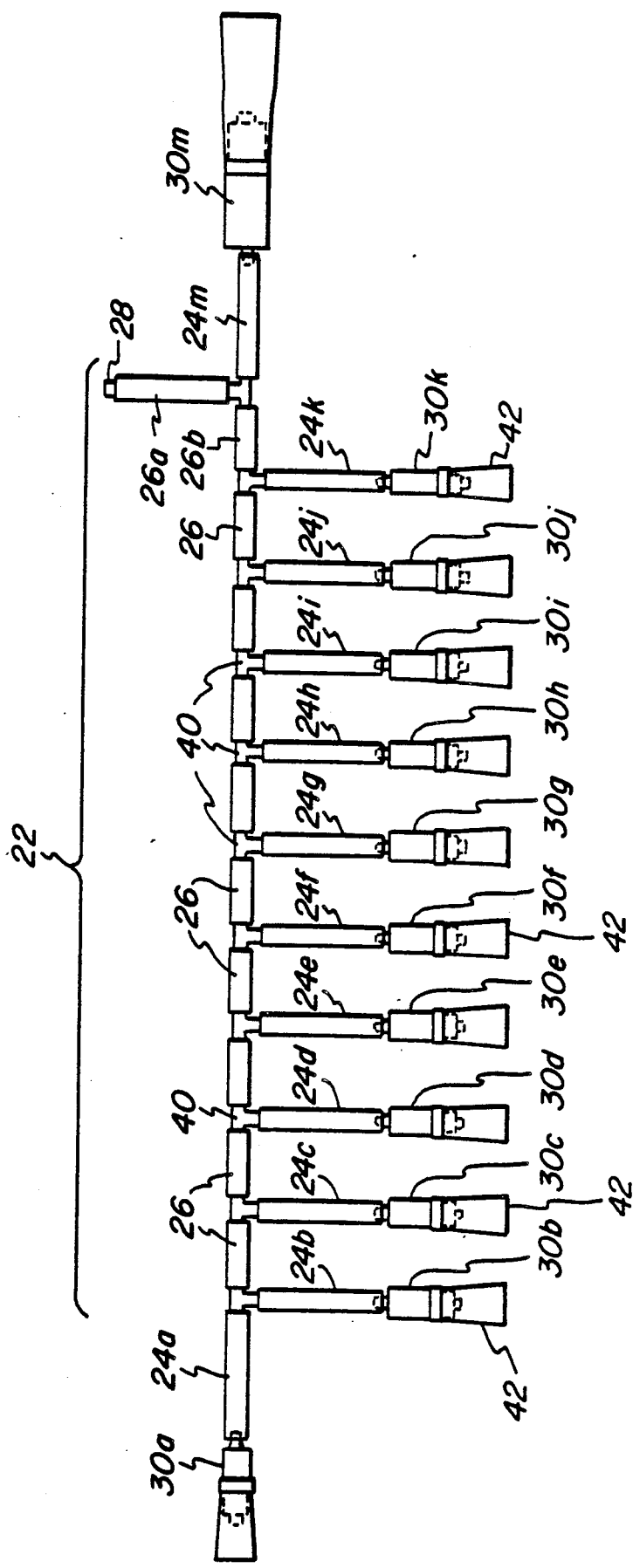
FIG. 2 is an elevational and expanded view of the preferred liquid sampling device of the invention.

As shown in FIG. 2, the preferred liquid sampling device 18 comprises a primary liquid conduit tube generally designated in its totality as 22 and made up of a number of lengths of tubing 26 connected together by suitable connectors 40 so as to form a continuous liquid conduit tube. Emanating from a number of spaced-apart areas of the primary conduit tube 22, most expediently at the connection points between tubing lengths 26 such as by using hollow T-shaped connectors 40, are a number of separate sample conduit tubes 24a through 24k and 24m made up of one or more tubing lengths. By virtue of the hollow T-connectors, one end of each of the sample conduit tubes is in separate liquid communication with the primary liquid conduit tube 22.

One end of the primary conduit tube 22, designated as 28, is adapted to be connected to the culture fluid flow line 20 through which culture fluid exiting from the culture unit 10 flows. The opposite end of primary liquid conduit tube 22 is closed, in this case by sample conduit tube 24a.

In the embodiment shown, each sample conduit tube 24 is open at its exit portion, and the exit portion is in sealed liquid communication with a conventional syringe device 30 comprised of a hollow bore or barrel section terminating in a sample opening, which is arranged in the exit portion of a sample conduit tube, and a movable plunger device liquid-tight within the hollow bore section. In the most preferred form of the invention, each syringe device 30 is enclosed within an envelope or bag of sterilizable flexible plastic material 42 which serves to prevent any risk of outside contamination entering the system as the syringe plunger is manipulated within the syringe bore, all of which is effected through the bag without opening the bag.

Normally, the liquid communication between the primary conduit tube 22 and the source of liquid to be sampled is such that control can be exercised over whether such communication will or will not be effected, e.g., as by a removable or releasable external clamp on segment 26a which open or closes its internal bore or by a valve mechanism at the point of connection or by other like means.

For sampling from the liquid source, liquid communication is first established between the liquid source and the primary conduit tube 22 (e.g., by releasing a clamp on tube segment 26a). Generally, it is desirable to first draw a portion of the liquid source into syringe 30m through tube segment 24m (and with clamping about segment 26b) in order to insure that the liquid actually sampled (e.g., through 30k) is free of bubbles or the like. To this end, syringe 30m generally is made larger than the other sample syringes. Thereafter, the clamp on segment 26b is removed and sample drawn through segments 26b and 24k into syringe 30k. The sample-containing syringe 30k is then either removed from sample conduit tube 24k (with clamping of tube 24k) or, alternatively, tube 24k can be clamped and the syringe "removed" by cutting tube 24k downstream of the clamp point. Following the sampling, the contents earlier drawn into syringe 30m can be flushed back into the liquid source through segments 24m and 26a, with clamping at segment 26b.

For the next sample, the same sequence is followed, with a first portion of liquid being drawn into syringe 30m, and then a sample portion drawn into syringe 30j through tube segment 24j. Sampling continues in this manner until all the sample conduit tubes and associated syringes are utilized.

As will be apparent, the order in which the syringes are used to sample the liquid source can be varied as desired and need not be sequential.

As is apparent, the arrangement of sample conduit tubes 24 along the length of primary conduit tube 22 can be in any convenient configuration, whether the sample conduit tubes all extend in the same direction from the primary conduit tube, or alternate one side and the other, or whether a sample conduit tube is used to cap off an end of the primary conduit tube or whether other means are used to end-close the primary tube. Still further, the syringes associated with the sample conduit tubes can be the same or different sizes depending upon sampling needs, and two or more samples can be taken at about the same time as needs may dictate.

Among the advantages of the sampling device of the invention is the ease with which it can be constructed and the fact that it can be constructed of materials which are easily and readily sterilizable. In the device shown in FIG. 2, for example, the lengths which make up the primary liquid conduit tube 22 and sample conduit tubes 24a–24k and 24m can be made of any suitable biologically inert material which is sufficiently rigid to maintain a liquid conduit bore therein and to permit interconnection using suitable connection devices, while at the same time being sufficiently flexible to permit bending and working as may be needed to effect connections. Typically, the conduits are made of a rubber or rubber-like material, with silicone rubber being preferred, but other polymeric materials also could be employed. Interconnection between lengths of primary conduit tube 22 and establishment of liquid communication between sample conduit tubes and the primary conduit tube can be effected through plastic (preferably nylon) connectors, with three-way hollow T-connectors being most preferred. Liquid-tight and aseptic sealing at the connector junctions is possible by arranging that the tube bores force fit over the connector prongs; however, it is preferred as an added measure of caution, and particularly where force-fitting is not achievable, to augment the seal by applying compressive force about the periphery of the tube end in which the connector prong lies, such as by the simple expedient of a tightly-wound and knotted thread.

The syringe devices can be made of plastic materials with the open sampling end suitably sized and shaped so as to be fittable within the open exit end of the sample conduit tube. Here again, a liquid-tight and aseptic seal can be achieved through a force-fit, preferably augmented by compressive force about the sample conduit tube periphery. As earlier noted, a suitable flexible plastic such as nylon film can be used to form a bag-like enclosure about the syringe and its point of connection to the sample conduit tube so as to insure maintenance of sterility when the syringe is being manipulated, through the envelope material, to withdraw a liquid sample.

Generally, the open end (e.g. 28) of the primary conduit tube which is to be arranged in liquid communication with the liquid source material to be sampled is closed upon initial construction, preferably using a sealing plug rather than metal clamping. The entire device can then be separately sterilized by any suitable means, including irradiation since no metal parts are involved. The sterilized sampling device is then attached to a principal or secondary flow line through which the liquid source material to be sampled flows or can be arranged to flow, by removing the sealing plug at 28 and forming a sterile connection thereat.

Figure 3:
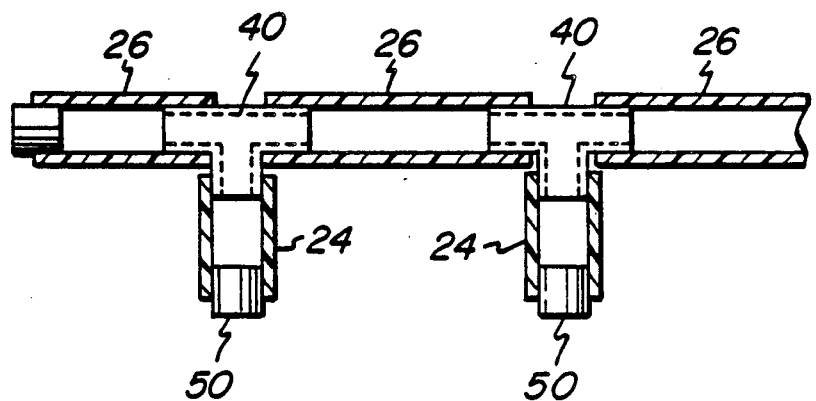
FIG. 3 is an elevational and expanded view of an alternative form of the liquid sampling device of the invention.

An alternative although less preferred embodiment of the invention is shown in FIG. 3. As in the earlier embodiment, a primary conduit tube 22 is formed from lengths of interconnected tubing 26 and, at the connection points, e.g., through use of a hollow T-connector 40, a plurality of separate sample conduit tubes 24 emanate from spaced-apart areas along the length of the primary conduit tube, and are in liquid communication therewith. In contrast to the embodiment of FIG. 2, the sample conduit tubes terminate in closed, sealed ends 50, such as by provision of an elastomeric plug at the exit end of the sample conduit tube. The primary conduit tube is closed at one end and the opposite end, although it can be initially closed for construction and sterilization of the device, is adapted to be opened for sterile connection to, and liquid communication with, a principal or secondary line through which the source liquid material to be analyzed flows or is arranged to flow. Samples are drawn through any particular sample conduit tube either by puncture of the closed exit end using a sterile needle and syringe or other collection device, or by removal of the closed exit end and sterile connection between the now open exit end and a suitable withdrawal and collection device. While perhaps not as completely free of risk of contamination during sampling as the system of the preferred embodiment, the system of the embodiment of FIG. 3 nevertheless represents a substantial improvement in the art since each sample conduit tube is invaded only once for sampling, and is then isolated or removed from the remaining sample conduit tubes by appropriate clamping and/or severing, as previously described. Obviously, any number of sample conduit tubes can be pre-arranged along the length of the primary conduit tube depending upon the anticipated number of samples to be taken.

While the sampling device of the invention was primarily designed as a means for periodically analyzing culture medium or culture fluid in an in vitro animal cell culture system, it should be apparent that the sampling device can be employed in any system or situation where need exists to make multiple samplings of a sterile liquid source material under conditions where risk of contamination to the entire system exists during the sampling process, including systems for analyzing fluids being provided to or withdrawn from a patient.

While the invention has been described with reference to particular embodiments, materials of construction, use environments, and the like, it will be apparent that these are for purposes of illustrating the fundamental aspects of the invention, and that various modifications can be made without departing from the scope and spirit of the invention, as defined in the appended claims.

What is claimed is:

1. A liquid sampling device for periodic removal of sample quantities of a sterile source liquid in a manner which reduces risk of introduction of contaminants to the source material, comprising a length of sterilizable primary liquid conduit tube, one end of which is closed to prevent escape of liquid therefrom and one end of which is adapted for liquid communication with a sterilized flow line through which said sterile source liquid flows or is arranged to flow; and, emanating from said sterilizable primary liquid conduit tube at pre-selected areas along its length, a plurality of separate sterilizable sample conduit tubes, each sample conduit tube being in liquid communication with said primary liquid conduit tube through one end of said sample conduit tube, and the other, exit end of said sample conduit tube being adapted to have a sample quantity of sterile source liquid aseptically withdrawn therethrough, by way of said primary liquid conduit tube and sample conduit tube, at least some of said exit ends of said sample conduit tubes being sealably affixed to and in liquid communication with the open sampling end of a sterilizable syringe comprised of a hollow barrel section in liquid communication with said open sampling end of said syringe and having an open end remote from said sampling end of said syringe, and a plunger, arranged in said remote end of said hollow barrel section and movable within said hollow barrel section, for enabling a predetermined quantity of sterile liquid sample to be collected in said hollow barrel section through said sample conduit tube, and wherein at least the portion of said syringe comprised of said plunger and said remote end of said hollow barrel section is enclosed within a flexible bag through which manipulation of said syringe plunger for sample withdrawal can occur without opening of the bag, the arrangement of said sample conduit tubes and primary liquid conduit tube being such as to permit one or more sample conduit tubes, after withdrawal of sample therethrough, to be isolated from the device while maintaining both liquid communication between the primary liquid conduit tube and the remaining sample conduit tubes, and end closure of the primary liquid conduit tube.

2. A method for periodically withdrawing a sample quantity of a sterile source liquid in a manner which reduces rick of introduction of contaminants to the source material, comprising:
    (a) aseptically affixing to a sterilized flow line through which said sterile source liquid flows, one end of a sterilized primary liquid conduit tube which is closed at its distal end such that liquid communication exists between said flow line and said primary liquid conduit tube, said primary liquid conduit tube having emanating therefrom at pre-selected areas along its length a plurality of separate sterilized sample conduit tubes each of which is in liquid communication with said primary liquid conduit tube through one end of said sample conduit tube, and the other, exit end of said sample conduit tube being adapted to have a sample quantity of sterile source liquid aseptically withdrawn therethrough, by way of said flow line, primary liquid conduit tube, and sample conduit tube, at least some of said exit ends of said sample conduit tubes being sealably affixed to an in liquid communication with the open sampling end of a sterilized syringe comprised of a hollow barrel section in liquid communication with said open sampling end of said syringe and having an open end remote from said sampling end of said syringe, and a plunger, arranged in said remote end of said hollow barrel section and movable within said hollow barrel section, for enabling a predetermined quantity of sterile liquid sample to be collected in said hollow barrel section through said sample conduit tube, and wherein at least the portion of said syringe comprised of said plunger and said remote end of said hollow barrel section is enclosed within a flexible bag through which manipulation of said syringe plunger for sample withdrawal can occur without opening of the bag,
    (b) manipulating said syringe plunger within said flexible bag so as to withdraw a sample quantity of said source liquid through said exit end of one of said sample conduit tubes and into the hollow barrel section of said syringe; and
    (c) isolating the sample conduit tube through which said sample has been withdrawn so as to remove it from liquid communication with said primary conduit tube while maintaining liquid communication between said primary liquid conduit tube and remaining sample conduit tubes and while maintaining end closure of said primary liquid conduit tube.

* * * * *